United States Patent [19]

Cragoe, Jr. et al.

[11] 4,100,294
[45] Jul. 11, 1978

[54] 5-(HYDROXY (SUBSTITUTED) METHYL)-2,3-DIHYDROBENZO FURAN-2-CARBOXYLIC ACID AND ITS DERIVATIVES

[75] Inventors: Edward J. Cragoe, Jr., Lansdale; Otto W. Woltersdorf, Jr.; William Hoffman, both of Chalfont, all of Pa.

[73] Assignee: Merck & Co., Inc., Rahway, N.J.

[21] Appl. No.: 747,840

[22] Filed: Dec. 6, 1976

[51] Int. Cl.$^2$ .................. C07D 307/82; A61K 31/18; A61K 31/34; A61K 31/425
[52] U.S. Cl. .......................... 424/275; 424/248.54; 424/267; 424/248.51; 424/248.51; 424/270; 424/285; 260/293.58; 260/302 H; 260/332.2 A; 260/346.22; 260/346.71; 544/153
[58] Field of Search ............... 260/346.2 R, 346.2 M, 260/302 H, 332.2 A, 293.58; 424/270, 275, 285, 267, 248.54; 544/153

[56] References Cited
FOREIGN PATENT DOCUMENTS
2,630,800 1/1977 Fed. Rep. of Germany.

OTHER PUBLICATIONS
Gaylord et al., Reduction With Complex Metal Hydrides, (1956), pp. 283–297.
Heymann et al., J. Am. Chem. Soc., vol. 73, 1951, pp. 5252, 5257 and 5264.

*Primary Examiner*—Alan L. Rotman
*Assistant Examiner*—Bernard Dentz
*Attorney, Agent, or Firm*—Michael C. Sudol, Jr.

[57] ABSTRACT

5-[Hydroxy(substituted)methyl]-2,3-dihydrobenzofuran-2-carboxylic acids, the pharmaceutically acceptable salt, ester and amide derivatives thereof and combinations of these compounds with antikaluretic agents are disclosed having diuretic-saluretic, uricosuric and antihypertensive activity.

14 Claims, No Drawings

5-(HYDROXY (SUBSTITUTED) METHYL)-2,3-DIHYDROBENZO FURAN-2-CARBOXYLIC ACID AND ITS DERIVATIVES

BACKGROUND OF THE INVENTION

This invention relates to certain benzofurans having diuretic-saluretic, uricosuric and antihypertensive pharmacological activity. Further, this invention relates to processes for the preparation of such compounds; pharmacological compositions comprising such compounds; and to methods of treatment comprising administering such compounds and compositions to patients (both human and animal) for the alleviation of symptoms associated with electrolyte imbalance and fluid retention such as edema associated with hypertension.

The compounds of this invention may be represented by the following generic structure:

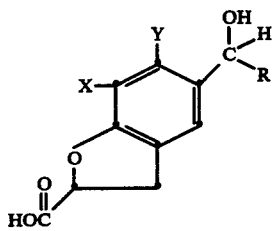

I wherein
X is halo (chloro, fluoro, bromo or iodo), methyl or hydrogen;
Y is halo (chloro, fluoro, bromo or iodo) or methyl;
X and Y can be joined to form a hydrocarbylene chain containing from 3 to 4 carbon atoms for example: 1,3-butadienylene;
R is aryl such as phenyl or mono or disubstituted phenyl wherein the substituent is halo, methyl, trifluoromethyl or methoxy; aralkyl such as benzyl or mono or dinuclear substituted aralkyl wherein the substituent is halo, methyl, methoxy or trifluoromethyl, or a heterocyclic group such as a 5 or 6 membered heterocyclic ring containing one or more atoms of oxygen, sulfur or nitrogen such as 3- or 2-thienyl, 3 or 2-furyl, 1,2,5-thiadiazolyl or substituted heterocyclics as above wherein the substituent is halo or methyl.

Also within the scope of the present invention are the pharmaceutically acceptable salt, ester and amide derivatives of the above described compounds.

For convenience, these compounds will be collectively referred to as "dihydrobenzofuran acids."

The pharmacological studies show that the instant products are effective diuretic, saluretic and uricosuric agents which can be used in the treatment of conditions associated with electrolyte and fluid retention in the treatment of hypertension. These compounds are able to maintain the uric acid concentration in the body at pretreatment levels or to even effect a decrease in the uric acid concentration when administered in therapeutic dosages in conventional vehicles.

Many of the presently available diuretics and saluretics have a tendency upon administration to induce hyperuricemia which may precipitate uric acid or sodium urate or both in the body which may cause from mild to severe cases of gout. The instant compounds of this invention now provide an effective tool to treat those patients (which includes humans and animals) requiring diuretic and saluretic treatment without incurring the risk of inducing gout. In fact, when used in appropriate doses, the compounds of this invention function as uricosuric agents.

The preferred benzofurans of the present invention are those compounds of Formula I wherein X is halo, preferably chloro, or methyl and Y is halo, preferably chloro, or methyl, and the pharmaceutically acceptable salts, ester and amide derivatives thereof.

More preferred benzofurans of the present invention are those preferred compounds of Formula I wherein R is

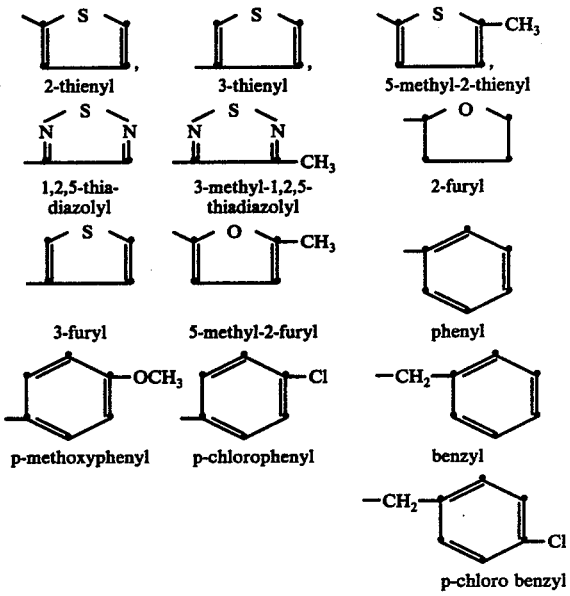

and X and Y are as defined above.

Still more preferred benzofurans of the present invention are those compounds of Formula II below:

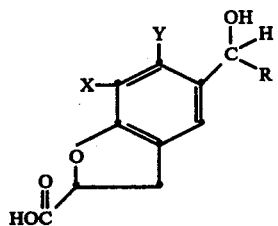

II wherein
X is chloro and
Y is chloro, and
R is as defined for the more preferred benzofurans above, and the pharmacologically acceptable salts, ester and amide derivatives thereof.

A still more preferred aspect of the invention are those compounds of Formula II wherein X and Y are both chloro and R is

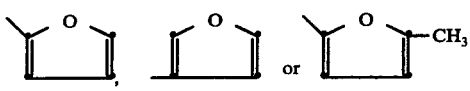

and the pharmaceutically acceptable salts, ester and amide derivatives thereof.

Several examples of specific compounds of this invention are 6,7-dichloro-2,3-dihydro-5-[hydroxy-(2-thienyl)-methyl]benzofuran-2-carboxylic acid;

6,7-dichloro-2,3-dihydro-5-[hydroxy-(2-furyl)-methyl]benzofuran-2-carboxylic acid;

6,7-dichloro-2,3-dihydro-5-hydroxy-[3-(1,2,5-thiadiazolyl)]methyl benzofuran-2-carboxylic acid;

6,7-dichloro-2,3-dihydro-5-($\alpha$-hydroxy-4-methoxybenzyl)benzofuran-2-carboxylic acid;

6,7-dichloro-2,3-dihydro-5-[(1-hydroxy-2-phenyl)-ethyl]benzofuran-2-carboxylic acid.

The preferred groups of compounds depicted above have especially good diuretic, saluretic, uricosuric and antihypertensive pharmacological activity.

The benzofurans of the present invention may be prepared essentially by the Reaction scheme shown below:

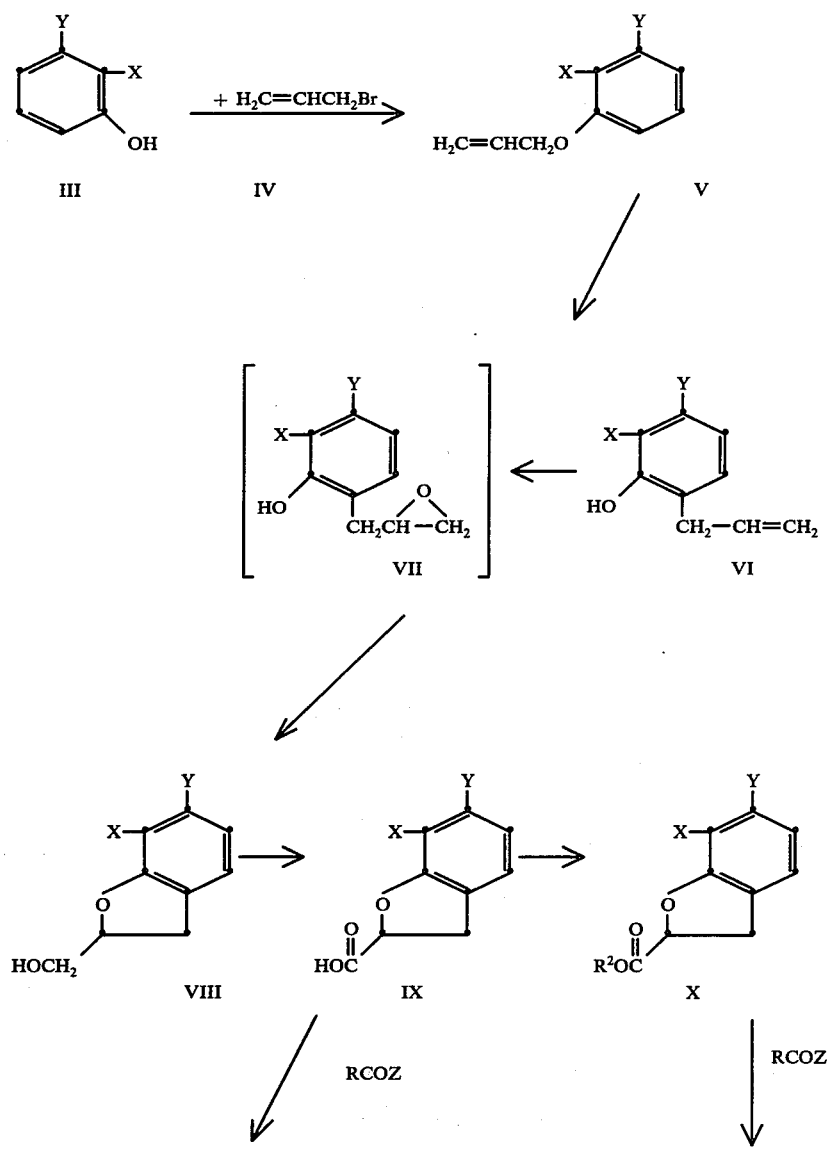

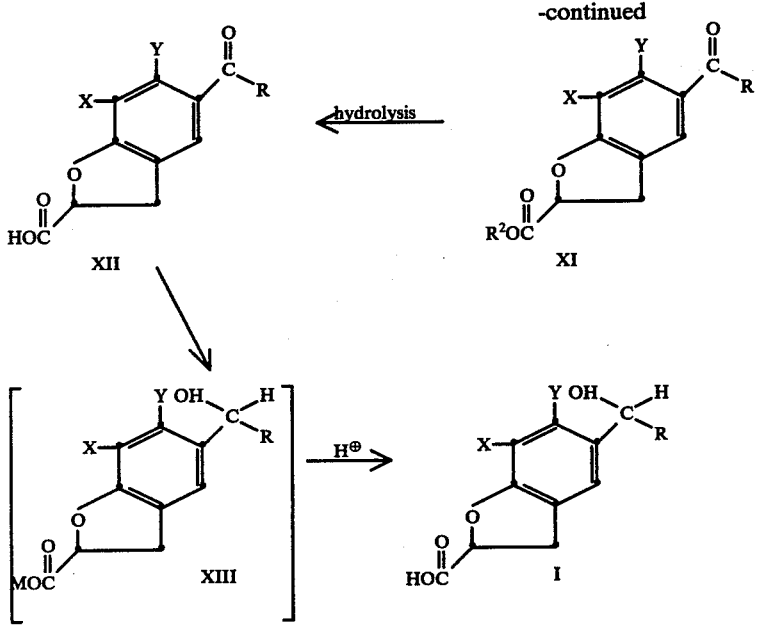

wherein X, Y and R are as defined, Z is halo and R² is lower alkyl (C₁₋₄) and M is an alkali metal cation.

In this reaction scheme, a 2,3-disubstituted-phenol (III) is treated with allyl bromide to yield the corresponding allyl ether (V). Typically the allyl bromide is employed in excess; in fact it may serve as the reaction solvent. Other solvents, provided they are compatible with the desired course of reaction may be employed, for example, ethanol, dimethylformamide and the like. Typically the reaction is conducted in the presence of a base such as sodium alkoxide, potassium carbonate and the like at a temperature in the range of from about 25° to about 100° C. and is substantially complete in from about 0.5 to about 2 hours. The Claisen rearrangement to obtain the 4-allyl compound (Formula VI) is effected by heating the reaction mixture at from about 100° to 220° C. The benzofuran nucleus (VIII) is obtained from the 4-allyl compound (VI) by treatment with a peracid such as m-chloroperbenzoic, peracetic acid and the like in a solvent such as methylene chloride, chloroform, acetic acid and the like at a temperature of from about 0° C. to the reflux temperature of the solvent wherein the epoxide (VII) which is initially formed cyclizes to (VIII). There are brackets around the epoxide of Formula (VII) to indicate that it is most generally not isolated and is an intermediate in this particular reaction step. Oxidation of the resulting hydroxymethyl-substituted-benzofuran (VIII) yields the benzofurancarboxylic acid (IX).

Typically this oxidation is effected by oxidizing agents such as chromic acid, potassium permanganate and the like; the temperature of the reaction being typically in the range of from about 0° C. to the reflux temperature of the solvent which is used.

The solvent can be any inert solvent that is not effected by the reaction.

Finally the benzofurancarboxylic acid compound (Formula IX) is converted to the dihydrobenzofurancarboxylic acid compounds of the instant invention (Formula I) by reacting said compound Formula (IX) or its lower alkyl (C₁₋₄) ester (X) under Friedel-Crafts conditions with a carboxylic acid halide of the formula: RCOZ wherein R has been previously defined and Z is halogen such as chloro or bromo, to yield the desired product directly or by hydrolysis of the resultant ester (XI). The lower alkyl ester (X) can be prepared from the acid (IX) by known esterification procedures. Suitable catalysts for the Friedel-Crafts type reaction on compounds of Formula (IX) are aluminum chloride, tin (IV) tetrachloride and the like. The reaction solvent and temperature are not critical inasmuch as any solvent which is inert to the acyl halide/benzofuran reactants may be employed. In this regard, suitable solvents include aliphatic and cycloaliphatic hydrocarbons such as heptane, cyclohexane, and the like; nitrohydrocarbons such as nitrobenzene and the like; and halogenated hydrocarbons such as carbon tetrachloride, methylene chloride, and the like are employable. The reaction is generally run until formation of the desired product (I) is complete, preferably from about 1 to 6 hours.

Typically the reaction is conducted from 0° C. to the reflux temperature of the particular solvent employed but temperatures up to about 100° maximum may be employed. Applicants have found that a better yield of final product (I) is obtained from compound (IX) by using no inert solvent but using a slight excess of the acyl halide.

Finally, in order to convert the dihydrobenzofurancarboxylic acid compound (XII) to the 5-[hydroxy(substituted)-methyl]-2,3-dihydrobenzofuran-2-carboxylic acid compounds of the instant invention (Formula I), Compound XII is reduced to an intermediate compound (XIII) which is then acidified to the desired product (Formula I). The reduction and acidification can and usually are carried out in the same vessel.

The reduction step is carried out by reacting Compound XII with a reducing agent which selectively reduces the carbonyls to alcohols when there is a carboxylic acid present. A preferable reducing agent is MBH₄ where M is an alkali metal cation such as particularly sodium borohydride or potassium borohydride.

The reduction is carried out in the presence of a solvent such as water or an alcohol. The use of a particular solvent is however not critical to the reaction.

The reduction is generally carried out anywhere from 1-24 hours and at a temperture of from 0° - 50° C. but preferably at ambient temperature.

The product (I) is then isolated from the reaction mixture where Compound (XIII) is formed as an intermediate by acidifying said reaction mixture with an inorganic acid such as an inorganic mineral acid as hydrochloric or sulfuric acid to precipitate the product (I) which is then isolated by filtration.

As previously mentioned, the nontoxic, pharmacologically acceptable salts of the acids of Formula (I) and (II) are within the scope of this invention. These salts include those of alkali metals, alkaline earth metals and amines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals, e.g., aluminum, iron and zinc.

Pharmaceutically acceptable salts can be formed from ammonia, primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, teramethylammonium hydroxide, tetraethylammonium hydroxide, benzyltrimethylammonium and the like. These salts are particularly useful as parenteral solutions because they are very soluble in pharmaceutical carriers such as water or alcohol.

Also included within the scope of this invention are the ester and amide derivatives of the instant products which are prepared by conventional methods well known to those skilled in the art. Thus, for example, the ester derivative may be prepared by the reaction of an dihydrobenzofuran-2-carboxylic acid of this invention with an alcohol, for example, with a lower alkanol such as methanol or ethanol. The amide derivatives may be prepared by converting the same acid to its corresponding acid chloride by treatment with thionyl chloride followed by treating said acid chloride with ammonia, an appropriate mono-lower alkylamine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding free acids of the present invention.

Of the non-toxic pharmaceutically acceptable salt, ester and amide derivatives of Formulae I and II, the preferred salts are those of ammonia, amines and of the alkali metals — principally sodium and potassium; the preferred esters are those derived from lower alkanols having from 1 to about 6 carbon atoms; the preferred amides are those derived from mono- and di-lower alkyl amines and hetero amines such as piperidine, morpholine and the like.

Although diuretics are often life-saving because of the above beneficial therapeutic effects, most of them have the disadvantage of causing the excretion of appreciable amounts of potassium ions. When an excessive loss of potassium ions occurs, a severe muscular weakness and feeling of extreme physical exhaustion results. The patient eliminates the unwanted sodium ions due to the action of the diuretic drugs but the undesired elimination of the potassium ions produces an imbalance that should not be allowed to persist.

This invention also involves co-administration of a dihydrobenzofurancarboxylic acid with a pyrazinoylguanidine either in the form of a salt and/or as a mixture with a hydrochloride salts of pyrazinoylguanidine, to thereby prevent the elimination of excessive amounts of potassium ions without altering or actually increasing the amount of sodium ions that are eliminated.

To achieve the beneficial results of this invention, the preferred pyrazinoylguanidine compound is N-amidino-3,5-diamino-6-chloropyrazinecarboxamide (amiloride) or its hydrochloride salt (amiloride hydrochloride) which is described in the literature and patented arts.

Another advantage of the N-amidino-3,5-diamino-6-chloropyrazinecarboxamide salts of the dihydrobenzofurancarboxylic acid diuretics is their insolubility which makes the salts' gastrointestinal absorption slower and more gradual providing a chemical method of achieving the same effect as microencapsulation.

The examples which follow illustrate the benzofuran products of the present invention and the methods by which they are prepared. However, the examples are illustrative only and it will be apparent to those having ordinary skill in the art that all the products embraced by the above-given description of the present invention may also be prepared in an analogous manner by substituting the appropriate starting materials for those set forth in the examples.

EXAMPLE 1

6,7-Dichloro-2,3-dihydro-5-[hydroxy-(2-thienyl)methyl]carboxylic acid

Step A: 2,3-Dichloro-6-allylphenol

A mixture of 2,3-dichlorophenol (35.5 g., 0.22 mole), allyl bromide (29.4 g., 0.24 mole) and potassium carbonate (33 g., 0.24 mole) in dimethylformamide (200 ml.) is vigorously stirred and heated at 55°-60° C. for one hour, poured into ice water, extracted with ether, washed with water and dried over magnesium sulfate. Evaporation of the ether leaves 2,3-dichlorophenyl allyl ether which is subjected to a Claisen rearrangement by heating at 250° C. for ten minutes. Distillation gives 36 g. of 2,3-dichloro-6-allylphenol which boils at 132°–4°/13 mm.

Elemental analysis for $C_9H_8Cl_2O$;
Calc.: C, 53.23; H, 3.97;
Found: C, 52.37; H, 3.86.

Step B: 6,7-Dichloro-2,3-dihydro-2-hydroxymethylbenzofuran

A stirred solution of sodium acetate (1 g.) in 40% peracetic acid (25 ml.) is cooled to 15° C. then treated dropwise with 2,3-dichloro-6-allylphenol. The reaction mixture is stirred at 25° C. for 48 hours, poured into excess aqueous sodium bicarbonate, extracted into ether, washed with aqueous sodium bicarbonate, water, aqueous ferrous sulfate, water, brine and dried over magnesium sulfate. Evaporation of the ether leaves 2,3-dichloro-6-(2,3-epoxypropyl)phenol which is rearranged by heating at 110° C. for ten minutes then distilled to give 10.4 g. of 6,7-dichloro-2,3-dihydro-2-hydroxymethylbenzofuran which boils at 130°/0.1 mm.

Elemental analysis for $C_9H_8Cl_2O_2$;
Calc.: C, 49.34; H, 3.68;
Found: C, 49.67; H, 3.74.

Step C: 6,7-Dichloro-2,3-dihydrobenzofuran-2-carboxylic acid

To a solution of 6,7-dichloro-2,3-dihydro-2-hydroxymethylbenzofuran (10.4 gm.) in acetone (200 ml.) cooled to 20° C. is added an oxidizing solution prepared from chromium trioxide (6.0 g.), concentrated sulfuric acid (5.3 ml.) and water (43 ml.) over a one-half hour period. The reaction mixture is stirred at 25° C. for 18 hours. The acetone layer is separated from the precipitated chromium salts, added to water (600 ml.) and extracted with ether (2 × 150 ml.). The ether extract is washed with water then extracted with aqueous sodium bicarbonate. Acidification of the basic solution gives 3.4 g. of 6,7-dichloro-2,3-dihydrobenzofuran-2-carboxylic acid which is purified by reprecipitation from aqueous sodium hydroxide with aqueous hydrochloric acid.

Elemental analysis for $C_9H_6Cl_2O_3$;
Calc.: Cl, 30.43; C, 46.38; H, 2.60;
Found: Cl, 30.29; C, 46.38; H, 2.62.

Step D: 6,7-Dichloro-2,3-dihydro-5-(2-thenoyl)-benzofuran-2-carboxylic acid

To a well stirred mixture of 6,7-dichloro-2,3-dihydrobenzofuran-2-carboxylic acid (2.6 g.) and thiophene-2-carbonyl chloride (4 ml.) protected from the atmosphere with a calcium chloride tube is added anhydrous aluminum chloride (6.0 g.) over a one-hour period. The reaction mixture is heated at 80°–90° C. for 3½ hours then poured into ice water (100 ml.) and hydrochloric acid (10 ml.). The product is extracted into ether, washed with water, then extracted into aqueous sodium bicarbonate (100 ml.) from which the sodium salt of the product precipitates. The sodium salt of the product is placed in a separatory funnel with dilute hydrochloric acid (100 ml.) and ether (100 ml.) and shaken until the solid dissolves. The ether solution is washed with water, brine, dried over magnesium sulfate and the ether distilled at reduced pressure. The 6,7-dichloro-2,3-dihydro-5-(2-thenoyl)benzofuran-2-carboxylic acid melts at 187° C. after crystallization from butyl chloride.

Elemental analysis for $C_{14}H_8Cl_2O_4S$;
Calc.: C, 49.00; H, 2.35;
Found: C, 48.72, H, 2.56.

Step E: 6,7-Dichloro-2,3-dihydro-5-[hydroxy-(2-thienyl)-methyl]benzofuran-2-carboxylic acid A magnetically stirred suspension of 3.4 g. (0.01 M) of 6,7-dichloro-2,3-dihydro-5-(2-thenoyl)-benzofuran-2-carboxylic acid and 100 ml. water is cooled to 5° C. in an icewater bath. A solution of 0.8 g. (0.0148 M) potassium borohydride and 20 ml. water is added dropwise to the above suspension over one-half hour. The resulting solution is stirred 2 hours at 25° C., filtered to remove some cloudiness and acidified with 6N HCl to give 6,7-dichloro-2,3-dihydro-5-[hydroxy-(2-thienyl)methyl]benzofuran-2-carboxylic acid as a yellow gum. The product is purified by precipitating it from 2N NaOH with 6N HCl. The aqueous solution is decanted from the gum which is triturated with 6N HCl to give a pale yellow solid. This solid is washed with water and air dried. It is then dried 24 hours at 25° C. and 1mm Hg over $P_2O_5$.

Elemental analysis for $C_{14}H_{10}Cl_2O_4S$;
Calc.: C, 48.71; H, 2.92;
Found: C, 48.62; H, 2.91.

EXAMPLE 2

6,7-Dichloro-2,3-dihydro-5-[hydroxy-2-furyl)methyl]-benzofuran-2-carboxylic acid Step A: 6,7-Dichloro-2,3-dihydro-5-(2-furoyl)-benzofuran-2-carboxylic acid To a well stirred mixture of 6,7-dichloro-2,3-dihydrobenzofuran-2-carboxylic acid (3.3 g.), furan-2-carbonylchloride (3.6 g.) and 200 ml methylene chloride, protected from the atmosphere with a calcium chloride tube is added anhydrous aluminum chloride (3.7 g.) over a one-half hour period. The reaction solution is stirred 18 hours at 25° C. and then refluxed for 1 hour. The solvent is removed and the residue added to ice water (200 ml.) and hydrochloric acid (20 ml.). The product is extracted into ether, washed with water, then extracted into aqueous sodium bicarbonate (200 ml.) from which the sodium salt of the product precipitates. The sodium salt of the product is placed in a separatory funnel with dilute hydrochloric acid (100 ml.) and ether (100 ml.) and shaken until the solid dissolves. The ether solution is washed with water, brine, dried over magnesium sulfate and the ether distilled at reduced pressure. The 6,7-dichloro-2,3-dihydro-5-(2-furoyl)benzofuran-2-carboxylic acid melts at 166° C. after crystallization from acetonitrile/n-butyl chloride.

Elemental analysis for $C_{14}H_8Cl_2O_5$;
Calc.: C, 51.40; H, 2.46;
Found: C, 51.59; H, 2.72.

Step B: 6,7-Dichloro-2,3-dihydro-5-[hydroxy-2-furyl)-methyl]benzofuran-2-carboxylic acid Following the procedure of Example 1, Step E, but substituting for the 6,7-dichloro-2,3-dihydro-5-(2-thenoyl)benzofuran-2-carboxylic acid used therein an equimolar amount of 6,7-dichloro-2,3-dihydro-5-(2-furoyl)benzofuran-2-carboxylic acid there is obtained 6,7-dichloro-2,3-dihydro-5-[hydroxy-2-furyl)methyl]-benzofuran-2-carboxylic acid.

EXAMPLE 3

6,7-Dichloro-2,3-dihydro-5-{hydroxy-[3-(1,2,5-thiadiazolyl)]-methyl}benzofuran-2-carboxylic acid Step A: 6,7-Dichloro-2,3-dihydrobenzofuran-2-carboxylic acid ethyl ester A solution of 6,7-dichloro-2,3-dihydrobenzofuran-2-carboxylic acid (70 g.) conc. sulfuric acid (2 ml.) and ethanol (250 ml.) is refluxed for 2 hours. The ethanol is distilled at reduced pressure and the residue is suspended in saturated sodium bicarbonate and extracted with ether. The ether solution is washed with brine, dried over magnesium sulfate and the ether distilled at reduced pressure, The 6,7-dichloro-2,3-dihydrobenzofuran-2-carboxylic acid ethyl ester is used without further purification in the following synthesis.

Step B: 6,7-Dichloro-2,3-dihydro-5-[3-(1,2,5-thiadiazolylcarbonyl)]benzofuran-2-carboxylic acid To a well stirred mixture of 6,7-dichloro-2,3-dihydrobenzofuran-2-carboxylic acid ethyl ester (17.5 g.) and 1,2,5-thiadiazole-3-carbonyl chloride (21.7 g.) protected from the atmosphere with a calcium chloride tube is added the anhydrous aluminum chloride (29.4 g.) over a one-half hour period. The reaction mixture is heated at 90°–95° C. for 6 hours, then poured into ice water (400 ml.) and hydrochloric acid (40 ml.). The esterified product is extracted into ether, washed with water, dried over magnesium sulfate and the ether distilled at reduced pressure. The residue was warmed (80°

C.) in 2.0N NaOH (100 ml.) for one hour to obtain the insoluble sodium salt of the product. The sodium salt of the product is placed in a separatory funnel with dilute hydrochloric acid (250 ml.) and ether (500 ml.) and shaken until the solid dissolves. The ether solution is washed with water, brine, dried over magnesium sulfate and the ether is distilled at reduced pressure. The 6,7-dichloro-2,3-dihydro-5[3-(1,2,5-thiadiazolylcarbonyl)-]benzofuran-2-carboxylic acid melts at 188° C. after recrystallization from acetonitrile.

Elemental analysis for $C_{12}H_6Cl_2N_2O_4S$;
Calc.: C, 41.75; H, 1.75; N, 8.12;
Found: C, 41.77; H, 1.89, N, 8.06.

Step C: 6,7-Dichloro-2,3-dihydro-5-{hydroxy-[3-(1,2,5-thiadiazolyl)]methyl}benzofuran-2-carboxylic acid Following the procedure of Example 1, Step E, but substituting for the 6,7-dichloro-2,3-dihydro-5-(2-thenoyl)benzofuran-2-carboxylic acid used therein an equimolar amount of 6,7-dichloro-2,3-dihydro-5-[3-(1,2,5-thiadiazolyl)]benzofuran-2-carboxylic acid there is obtained 6,7-dichloro-2,3-dihydro-5-{hydroxy[3-(1,2,5-thiadiazolyl)]methyl}benzofuran-2-carboxylic acid.

EXAMPLE 4

Starting with 6,7-dichloro-2,3-dihydrobenzofuran-2-carboxylic acid but substituting equimolar amounts of the following acyl halides in place of thiophene-2-carbonyl chloride in Step D of Example 1 and following the procedures of Steps D and E there is obtained a corresponding amount of the appropriate end product listed.

| ACID CHLORIDE | END PRODUCT |
|---|---|
| 5-methylthiophene-2-carbonyl chloride | 6,7-dichloro-2,3-dihydro-5-[hydroxy(5-methyl-2-thienyl)methyl]benzofuran-2-carboxylic acid |
| thiophene-3-carbonyl chloride | 6,7-dichloro-2,3-dihydro-5-[hydroxy(3-thienyl)methyl]-benzofuran-2-carboxylic acid |
| furan-3-carbonyl chloride | 6,7-dichloro-2,3-dihydro-5-[hydroxy(3-furyl)methyl]-benzofuran-2-carboxylic acid |
| 5-methylfuran-2-carbonyl chloride | 6,7-dichloro-2,3-dihydro 5-[hydroxy(5-methyl-2-furyl)-methyl]benzofuran-2-carboxylic acid |

EXAMPLE 5

Where in Example 1, Step D, there is substituted for the 6,7-dichloro-2,3-dihydrobenzofuran-2-carboxylic acid an equivalent amount of 2,3-dihydro-6,7-dimethyl-benzofuran-2-carboxylic acid, 2,3-dihydro-6-methyl-benzofuran-2-carboxylic acid, 6-chloro-2,3-dihydrobenzofuran-2-carboxylic acid or 6-chloro-2,3-dihydro-7-methylbenzofuran-2-carboxylic acid respectively and following procedures of Steps D and E, the following compounds of this invention are obtained, respectively:

2,3-dihydro-6,7-dimethyl-5-[hydroxy-(2-thienyl)methyl]-benzofuran-2-carboxylic acid;

2,3-dihydro-6-methyl-5-[hydroxy-(2-thienyl)methyl]-benzofuran-2-carboxylic acid;

6-chloro-2,3-dihydro-5-[hydroxy-(2-thienyl)methyl]-benzofuran-2-carboxylic acid;

6-chloro-2,3-dihydro-7-methyl-5-[hydroxy-(2-thienyl)methyl]-benzofuran-2-carboxylic acid;

EXAMPLE 6

6,7-Dichloro-2,3-dihydro-5-(α-hydroxy-4-methoxybenzyl)-benzofuran-2-carboxylic acid Step A: 6,7-Dichloro-2,3-dihydro-5(4-methoxybenzoyl)benzofuran-2-carboxylic acid Following the procedure of Example 2, Step A but using an equivalent amount of anisoyl chloride in place of furan-2-carbonyl chloride used in Example 2, Step A, there is produced an equivalent amount of 6,7-dichloro-2,3-dihydro-5-(4-methoxybenzoyl)benzofuran-2-carboxylic acid.
M.P. = 187° C Elemental analysis for $C_{17}H_{12}Cl_2O_5$;
Calc.: C, 55.60; H, 3.29; Cl, 19.31;
Found: C, 55.67; H, 3.35; Cl, 18.99.

Step B: 6,7-Dichloro-2,3-dihydro-5-(α-hydroxy-4-methoxybenzyl)benzofuran-2-carboxylic acid Following the procedure of Example 1, Step E but substituting for the 6,7-dichloro-2,3-dihydro-5-(2-thenoyl)-benzofuran-2-carboxylic acid used therein and equimolar amount of 6,7-dichloro-2,3-dihydro-5(4-methoxybenzoyl) benzofuran-2-carboxylic acid there is obtained 6,7-dichloro-2,3-dihydro-5-(α-hydroxy-4-methoxybenzyl)benzofuran-2-carboxylic acid.

EXAMPLE 7

6,7-Dichloro-2,3-dihydro-5-[(1-hydroxy-2-phenyl)ethyl]-benzofuran-2-carboxylic acid Step A: 6,7-Dichloro-2,3-dihydro-5-phenylacetyl benzofuran-2-carboxylic acid Following the procedure of Example 3B but using an equivalent amount of phenyl acetyl chloride in place of 1,2,5-thiadiazole-3-carbonyl chloride and using carbon disulfide as a solvent there is produced an equivalent amount of 6,7-dichloro-2,3-dihydro-5-phenylacetyl benzofuran-2-carboxylic acid, m.p. 146° C.

Elemental analysis for $C_{17}H_{12}Cl_2O_4$;
Calc.: C, 58.14; H, 3.44;
Found: C, 58.12, H, 3.67.

Step B: 6,7-Dichloro-2,3-dihydro-5-[(1-hydroxy-2-phenyl)ethyl]benzofuran-2-carboxylic acid Following the procedure of Example 1, Step E but using an equivalent amount of 6,7-dichloro-2,3-dihydro-5-phenylacetyl benzofuran-2-carboxylic acid there is obtained 6,7-dichloro-2,3-dihydro-5-[(1-hydroxy-2-phenyl)-ethyl]benzofuran-2-carboxylic acid.

Also as mentioned previously, these compounds are able to maintain the uric acid concentration in the blood at pretreatment levels or even cause a decrease in uric acid concentration. The presence of excess uric acid in the blood can lead to crystallization of uric acid and uric acid salts in the joints causing gout. In addition hyperuricemia in conjunction with hyperlipidemia has been implicated in increasing the risk of sustaining cardiovascular heart disease.

The compounds of this invention can be administered to patients (both animal and human) in conventional vehicles as, for example, by oral administration in the form of a tablet or by intravenous injection. In addition, the compounds may be formulated into suppositories or as a salve for topical administration or they may be administered sublinqually. Also, the daily dosage of the products may be varied over a wide range as for example, in the form of scored tablets containing 0.25, 1, 5, 10, 25, 50, 100, 150, 200, 250 and 500 milligrams of the active ingredient for the symptomatic adjustment of the dosage to the patient to be treated. These dosages are well below the toxic or lethal dose of the products.

A suitable unit dosage form of the product of this invention can be administered by mixing 25 mg. of a dihydrobenzofuran or a suitable salt, ester or amide derivative thereof of the present invention with 174 mg. of lactose and 1 mg. of magnesium stearate and placing the 200 mg. mixture into a No. 1 gelatin capsule. Similarly by employing more of the active ingredient and less lactose, other dosage forms can be put in No. 1 gelatin capsules and should it be necessary to mix more than 200 mg. of ingredients together larger capsules may be employed. Compressed tablets, pills or other desired unit dosages can be prepared to incorporate the compounds of this invention by conventional methods and if desired can be made up as elixirs or as injectable solutions by methods well known to pharmacists.

An effective amount of the product is ordinarily supplied at a unit dosage level of from about 0.003 mg. to about 10 mg./kg. of body weight of the patient. Preferably the range is from about 0.01 mg. to about 1.5 mg./kg. with a most preferred dose being about 0.07 to 0.35 mg./kg. of body weight. The unit dose can be administered as infrequently as twice per week to as frequently as 3 times per day.

It is also within the scope of this invention to combine two or more of the compounds of this invention into a unit dosage form or to combine one or more of the compounds of this invention with other known diuretics and saluretics or with other desired therapeutic and/or nutritive agents in dosage unit form.

The present invention embraces such compositions administration to patients, preferably by oral administration, wherein the potassium conserving diuretic, N-amidino- 3,5-diamino-6-chloropyrazinecarboxamide hydrochloride, hereinafter referred to as amiloride hydrochloride is present as a physical mixture in combination with the dihydrobenzofurans of the present invention. The present invention embraces compositions wherein the molar ratio of the dihydrobenzofuran to amiloride hydrochloride ranges from about 50:1 to 1:1. The preferred ratios of the dihydrobenzofuran to amiloride hydrochloride ranges from 25:1 to 1:1.

EXAMPLE 8

| Dry-filled capsules containing 25 mg. of active ingredients per capsule | |
|---|---|
| 6,7-Dichloro-2,3-dihydro-5-[hydroxy-(2-thienyl)methyl]-benzofuran-2-carboxylic | 25 mg. |
| Lactose | 174 mg. |
| Magnesium stearate | 1 mg. |
| Capsule (Size No. 1) | 200 mg. |

The 6,7-dichloro-2,3-dihydro-5-[hydroxy-(2-thienyl)-methyl]-benzofuran-2-carboxylic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules are prepared by replacing the active ingredient of the above example by the sodium, diethanolamine, and triethanolamine salt thereof, respectively.

What is claimed is:
1. A compound having the formula:

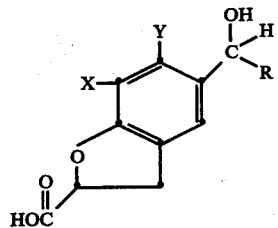

wherein
X is halo, methyl or hydrogen;
Y is halo or methyl and
X and Y can be combined to form a hydrocarbylene radical of from 3 to 4 carbon atoms;
R is phenyl or mono or disubstituted phenyl wherein the substituent is halo, methyl, trifluoromethyl or methoxy; benzyl or mono- or di-nuclear substituted benzyl wherein the substituent is halo, methyl, methoxy or trifluoromethyl, 2-thienyl, 3-thienyl, 5-methyl-2-thienyl, 1,2,5-thiadiazolyl, 3-methyl-1,2,5-thiadiazolyl, 2-furyl, 3-furyl, and 5-methyl-2-furyl, and the non-toxic pharmaceutically acceptable salt, lower alkyl ester and the mono or di lower alkyl, piperidine and morpholine amides thereof.

2. A compound of claim 1 wherein X is halo or methyl and Y is halo or methyl.

3. A compound of claim 2 wherein X nd Y are halo.

4. A compound of the formula

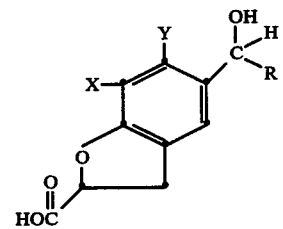

wherein
X is halo, methyl or hydrogen;
Y is halo or methyl;
X and Y can be combined to form a hydrocarbylene radical of from 3 to 4 carbon atoms;
R is selected from the group consisting of 2-thienyl, 3-thienyl, 5-methyl-2-thienyl, 1,2,5-thiadiazolyl, 3-methyl-1,2,5-thiadiazolyl, 2-furyl, 3-furyl, 5-methyl-2-furyl, phenyl, p-methoxyphenyl, p-chlorophenyl, benzyl and p-chlorobenzyl and the non-toxic pharmaceutically acceptable salt, lower alkyl ester and the mono or di lower alkyl, piperidine and morpholine amides thereof.

5. The compound of claim 4 wherein X and Y are both chloro.

6. A compound of claim 4 wherein X and Y are chloro and R is 2-thienyl, 3-thienyl, 5-methyl-2-thienyl, 2-furyl, 3-furyl or 5-methyl-2-furyl.

7. A pharmaceutical composition comprising a therapeutically effective amount of a compound of the formula of

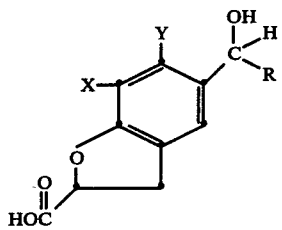

wherein
  X is halo, methyl or hydrogen;
  Y is halo or methyl,
  X and Y can be combined to form a hydrocarbylene radical of from 3 or 4 carbon atoms,
  R is phenyl or mono or disubstituted phenyl wherein the substituent is halo, methyl, trifluoromethyl or methoxy; benzyl or mono- or di-nuclear substituted benzyl wherein the substituent is halo, methyl, methoxy or trifluoromethyl, 2-thienyl, 3-thienyl, 5-methyl-2-thienyl, 1,2,5-thiadiazolyl, 3-methyl-1,2,5-thiadiazolyl, 2-furyl, 3-furyl, and 5-methyl-2-furyl, and the non-toxic pharmaceutically acceptable salt, lower alkyl ester and the mono or di lower alkyl, piperidine and morpholine amides thereof and a pharmaceutically acceptable carrier.

8. A pharmaceutical composition according to claim 7 wherein X and Y are both chloro.

9. A pharmaceutical composition comprising a therapeutically effective amount of a compound of the formula:

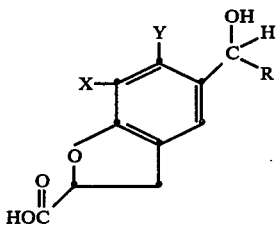

wherein
  X is chloro;
  Y is chloro; and
  R is selected from the group consisting of 2-thienyl, 3-thienyl, 5-methyl-2-thienyl, 1,2,5-thiadiazolyl, 3-methyl-1,2,5-thiadiazolyl, 2-furyl, 3-furyl, 5-methyl-2-furyl, phenyl, p-methoxyphenyl, p-chlorophenyl, benzyl and p-chlorobenzyl and the non-toxic pharmaceutically acceptable salt, lower alkyl ester and the mono or di lower alkyl, piperidine and morpholine amides thereof and a pharmaceutically acceptable carrier.

10. A pharmaceutical composition of claim 9 wherein the said compound is 6,7-dichloro-2,3-dihydro-5-[hydroxy-(2-thienyl)methyl]-2-carboxylic acid.

11. A method of treatment of edema associated with hypertension comprising the administration of a therapeutically effective amount in unitary dosage form of a compound having the formula of:

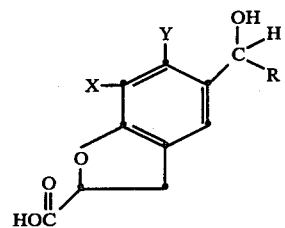

wherein
  X is halo, methyl or hydrogen;
  Y is halo or methyl;
  X and Y can be combined to form a hydrocarbylene radical of from 3 to 4 carbon atoms;
  R is phenyl or mono or disubstituted phenyl wherein the substituent is halo, methyl, trifluoromethyl or methoxy; benzyl or mono- or di-nuclear substituted benzyl wherein the substituent is halo, methyl, methoxy or trifluoromethyl, 2-thienyl, 3-thienyl, 5-methyl-2-thienyl, 1,2,5-thiadiazolyl, 3-methyl-1,2,5-thiadiazolyl, 2-furyl, 3-furyl, and 5-methyl-2-furyl, and the non-toxic pharmaceutically acceptable salt, lower alkyl ester and the mono or di lower alkyl, piperidine and morpholine amides thereof.

12. A method of treatment of edema associated with hypertension according to claim 11 comprising the administration to a patient of from 0.01 mg. to 10 mg./kg. of body weight of the patient of a compound of claim 11 wherein X and Y are both chloro.

13. A method of treatment of edema associated with hypertension comprising the administration to a patient of from 0.01 mg. to 10 mg./kg. of body weight of the patient of a compound having the formula:

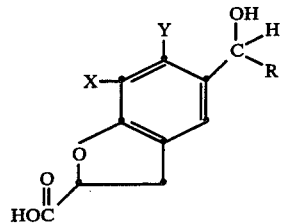

wherein
  X is chloro;
  Y is chloro; and
  R is selected from the group consisting of 2-thienyl, 3-thienyl, 5-methyl-2-thienyl, 1,2,5-thiadiazolyl, 3-methyl-1,2,5-thiadiazolyl, 2-furyl, 3-furyl, 5-methyl-2-furyl, phenyl, p-methoxyphenyl p-chlorophenyl, benzyl and p-chlorobenzyl and the non-toxic pharmaceutically acceptable salt, lower alkyl ester and the mono or di lower alkyl, piperidine and morpholine amides thereof.

14. A method of treatment of claim 13 wherein the compound to be administered is 6,7-dichloro-2,3-dihydro-5-[hydroxy-(2-thienyl)methyl]benzofuran-2-carboxylic acid.

* * * * *